(12) United States Patent
Meeten et al.

(10) Patent No.: US 7,622,916 B2
(45) Date of Patent: Nov. 24, 2009

(54) DETECTOR

(75) Inventors: Gerald Meeten, Ware (GB); Michael Paul Barrett, Histon (GB)

(73) Assignee: Schlumberger Technology Corporation, Cambridge, MA (US)

( * ) Notice: Subject to any disclaimer, the term of this patent is extended or adjusted under 35 U.S.C. 154(b) by 0 days.

(21) Appl. No.: 11/613,877

(22) Filed: Dec. 20, 2006

(65) Prior Publication Data

US 2008/0150521 A1 Jun. 26, 2008

(51) Int. Cl.
*G01N 27/83* (2006.01)
(52) U.S. Cl. .................................. 324/221; 324/220
(58) Field of Classification Search ............ 324/207.17, 324/207.18, 207.22, 220, 221, 228, 239, 324/240, 326–329, 67; 166/254.2, 255.1
See application file for complete search history.

(56) References Cited

U.S. PATENT DOCUMENTS 5,119,023 A * 6/1992 Lloyd ..................... 324/239
6,437,573 B1 * 8/2002 Golder et al. ............. 324/329
6,768,299 B2 * 7/2004 Almaguer .................. 324/221
2003/0117134 A1 6/2003 Almaguer

FOREIGN PATENT DOCUMENTS

EP 0 697 497 A1 2/1996
EP 1 302 624 A1 4/2003

OTHER PUBLICATIONS

Wilson, John W. et al Residual magnetic field sensing for stress measurement Sensors and Actuators A, 2006, doi:10.1016/j.sna.2006.08.010.

* cited by examiner

*Primary Examiner*—Kenneth J Whittington
(74) *Attorney, Agent, or Firm*—James McAleenan; Jody Lynn DeStefanis; Dale Gaudier

(57) ABSTRACT

A casing position locator for detecting structural features of a borehole casing, the locator including: a plurality of field generators for generating respective dynamic magnetic fields which combine to provide a dynamic test magnetic field to interact with the casing, where the test field includes a magnetic field null point located where the respective dynamic magnetic fields substantially cancel each other out; and a sensor for detecting a change in the position of the null point, relative to the sensor, due to the interaction.

17 Claims, 3 Drawing Sheets

DETECTOR

BACKGROUND

The present invention relates to a casing position locator for detecting structural features of a borehole casing.

The borehole of a well, such as an hydrocarbon well, is often lined with a borehole casing which extends along the length of the borehole or sections of it. Borehole casings are generally formed of a series of individual tubes jointed together, e.g. by collars, to form a continuous borehole casing.

However, it is often necessary to perform maintenance, repair or modifications of the casing—either the joints or the respective tubes making up the casing. In order to do this, the relevant portion of the casing to be e.g. repaired of maintained must be accurately located. This is usually achieved by using a casing collar locator (CCL) to locate the respective collars.

The conventional casing collar locator (CCL) is a passive device generally comprising two permanent magnets 101, 102 and at least one detecting coil 103, as shown in e.g. FIG. 1. In use, the permanent magnets 101, 102 are arranged so that each magnet presents the same pole to the other—in the example shown in FIG. 1 each magnet is presenting its "south" pole to the other magnet. The detecting coil 103 for detecting a change in the local magnetic field is located between the magnets 101, 102. The detecting coil 103 is connected to a detector 104 for detecting an electromotive force (emf) induced in the coil 103. The amplitude of induced emf in the coil 103 is proportional to the rate of change of magnetic flux through it.

The conventional way to use such a CCL is to lower it down a borehole casing on a wireline (or slickline). The magnetic flux linking the magnets to the turns of the coil depends on the local magnetic properties of the casing. The flux is time-independent if the CCL is stationary—hence no emf is generated in the coil.

If the CCL is moved along the casing and there is no time-variation of the flux caused by a spatial variation of the casing's magnetic properties there is also no emf induced in the coil. If, however, there is a spatial variation of the casing's magnetic properties e.g. owing to the proximity of a casing collar, the flux will vary in time proportionally to the speed of the CCL along the casing, and a detectable emf will be induced in the coil when the tool is close to a collar.

Detecting the emf induced in the coil then provides an indication that e.g. a collar is present at that location.

When collars are located, the corresponding length of dispensed wireline is recorded, thereby giving an indication of the distance to each respective collar. The number and relative location of the detected casing joints are then compared with the well reference logs. An example of such a CCL is given in European patent application publication number EP-A-0697497.

However, a conventional CCL will also detect residual or permanent magnetization of parts of the casing structure, or surrounding environment, as it moves rapidly by them. Such detections may subsequently (and erroneously) be treated as a collar or some other structural feature of the borehole casing. Such spurious or specious detections can be costly and time-consuming. Furthermore, because of the use of permanent magnets, the conventional CCL is prone to attracting magnetic detritus. As the magnets cannot be readily de-energized, the detritus is difficult to remove.

Also, the magnetic permeability of materials such as steels depends on the stress and strain to which they are subject Residual magnetic field sensing for stress measurement (J W Wilson, G Y Tian, and S Barrans, Sensors and Actuators A, (2006)—electronic reference: doi10.1016/j.sna.2006.08.010). This will give rise to time-variations of the detected magnetic flux extra to the magnetic flux changes arising from the proximity of the collar. This will affect all methods that use quasi-static magnetic fields, whether arising from permanent magnets, the geomagnetic field, or the remanant magnetization of the casing.

The sensitivity of the conventional CCL is dependent on the speed at which it moves because it is sensitive to the rate of change of flux. In the past, rapid moving wireline tools have been used in conjunction with these conventional CCLs to e.g. maintain borehole casings, and so this has not proved problematic.

More recently however, it has been proposed to use alternatives to wireline tools, such as autonomous wellbore robots (AWRs), to e.g. maintain borehole casings. However, AWRs tend to move more slowly through borehole casings than wireline tools. Therefore, using a conventional CCL with a slow moving AWR is undesirable because the slow movement reduces the sensitivity of the conventional CCL. Indeed, the AWR may move so slowly that the sensitivity of the conventional CCL may prevent it from accurately indicating the location of e.g. casing collars.

EP-A-1302624 discloses another conventional CCL which replaces the sense coil with a giant magnetoresistive, sometimes referred to as a giant magnetoresistance, (GMR) digital field sensor, thereby eliminating the velocity dependence. However, GMR devices are sensitive to the absolute magnitude of local magnetic fields, and so a conventional GMR CCL is prone to providing specious indications as to the presence of a casing feature such as a collar.

SUMMARY

Accordingly, the present invention provides a casing position locator for detecting the structural features of a borehole casing, where the locator includes: a plurality of field generators for generating respective dynamic magnetic fields, e.g. time-varying, which combine in use to provide a dynamic test magnetic field to interact with the casing, wherein the test field includes a magnetic field null point where the respective dynamic magnetic fields substantially cancel each other out; and a sensor for detecting in use a change in the position of the null point, relative to the sensor, due to said interaction.

In use the locator is sensitive to magnetic reluctance changes in the casing independent of the rate at which the locator moves along the casing because the generators preferably generate respective time-varying magnetic fields. Consequently, there is no need to move the locator rapidly along the borehole casing.

The fields generated by the respective field generators are provided so that a magnetic field null point is provided in the test magnetic field resulting from the combination of each of the generated fields. By "null point" it is meant the point or region in a magnetic field where the field has a minimum value (which could be a point or region where the field is zero, or substantially zero) e.g. provided by two or more fields substantially cancelling each other out. For example, according to the present invention two similar magnetic field generators (e.g. similarly wound electromagnetic coils) may be provided for generating respective time-varying magnetic fields can be arranged (e.g. to have electric currents flowing in opposite directions in the coils) so that in use a region between them is maintained at a minimum (preferably substantially zero) magnetic field value, even though at other regions between the generators there is a non-zero resultant time-varying field, for example.

The sensor can be located anywhere in the resultant field which permits flux linkage between the field generators and the sensor. If the magnetic environment of the locator is altered so that the magnetic environment of the locator becomes asymmetric (e.g. in the permeability of the borehole casing, such as the presence of a casing closer to one generator), then the relationship between the generated fields is altered and the position of the null point may be altered with respect to the generators and/or the sensor. In other words, one of the generated magnetic fields may be e.g. attenuated more than the or each other field, and the null point in the resultant magnetic field is caused to shift position (relative to the generators and/or the sensor).

A sensor located in the magnetic field, either proximal to or distal from the null point, can detect a change in the magnetic field distribution, indicating that the null point has changed position. This indication provides evidence of the presence of e.g. a casing collar.

Preferably, the null point is located between the respective field generators when the locator is in a substantially symmetric magnetic environment.

Preferably, the sensor is located in the region of the null point when the magnetic environment of the locator is symmetric so that the sensor output it is a minimum, preferably substantially zero. However, such a location of the sensor is not essential. Nonetheless, where the sensor is so located, any asymmetry in the magnetic environment will cause the null point to shift away from the sensor. The magnetic field detected by the sensor therefore results in a non-minimum (e.g. non-zero) signal output by the sensor indicating the presence of a magnetically asymmetric environment—e.g. the presence of a casing collar.

Preferably, the sensor can output a signal which indicates the relative strength of the detected magnetic field. The sensor may output a signal directly proportional to the strength of the detected magnetic field.

One or more generators is preferably controllable to provide a dynamic magnetic field on the basis of a signal output by the sensor, which indicates the strength of the detected magnetic field. In this way it is possible to "preset" the location of the null point at the sensor, e.g. prior to using the locator.

Preferably, the null point can be maintained substantially in one position (relative to the field generators and/or the sensor) by adjusting the respective generated field of one or more of the generators on the basis of a signal output by the sensor which indicates that the null point has shifted position (relative to the field generators and/or the sensor). Monitoring the control signal to the or each generator gives an indication of the asymmetry in the magnetic environment of the locator, e.g. the presence of a collar locator.

The sensitivity of the present invention can be increased by using this method, where independently of the type of sensor used, the currents in the electromagnets are adjustable e.g. automatically to maintain a null signal from the sensor. So, for example, the measurable difference between the currents of the two electromagnets is then a measure of the asymmetry of magnetization between each electromagnet and the sensor. This method can be used with any dynamic field generator and any sensor.

Preferably, each of the one or more of the magnetic field generators includes an electromagnetic coil. Where two or more coils are provided, it is preferred that the respective coils are, as far as possible, substantially identical so that the respective fields generated by the coils are substantially identical. Two such coils may be provided, mutually arranged to provide the respective magnetic fields in opposition preferably to provide a null point in the resultant magnetic field between the generators.

Preferably, one or more of the coils includes a magnetizable core, for example a soft iron core, or a high magnetic permeability ferrite core.

The sensor may include any device capable of accurately detecting a magnetic field, or a change in a magnetic field, and outputting a signal corresponding to the magnetic field, or the change in the magnetic field.

The sensor may include an electromagnetic sense coil. Preferably, the sense coil also includes a magnetizable core, which may be a soft iron core or it may be a high magnetic permeability ferrite core.

The sensor may be any "solid state" device capable of accurately detecting a magnetic field, or a change in a magnetic field, and outputting a signal corresponding to the magnetic field, or the change in the magnetic field. For example, the sensor could include a flux-gate detector. The sensor may include a semiconductor device for detecting magnetic fields, such as a GMR device or a Hall effect device. The sensor may include an optical apparatus e.g. one which uses Faraday rotation to detect the magnetic field (and/or a change in the magnetic field) and which outputs a signal indicative of such.

A plurality of sensors may be provided in a locator according to the present invention, whereby the respective signals may provide more accurate information about the respective locations of features of the borehole casing. A plurality of sensors may be provided as a circumferential array, whereby each sensor is preferably located in use close to a respective portion of the borehole casing.

Where a plurality of sensors is provided, it is preferred that each sensor is located at a respective substantial null point, e.g. of a null plane provided between two opposing magnetic field generators.

Preferably, each respective generated dynamic magnetic field is a time-varying magnetic field (i.e. an oscillating magnetic field) of a predetermined frequency. A preferred frequency of oscillation of each magnetic field is between 0.1 Hz and 10 kHz. However, the frequency may be between 0.1 Hz and 1 kHZ, or it may be between 0.1 Hz and 100 Hz.

Each (oscillating) generated dynamic magnetic field oscillates at the same frequency to provide a null point which is stationary relative to the field generators, when the locator is in a symmetric magnetic environment.

Preferably, the locator includes a detector for detecting in the output signal of the sensor a signal having the same frequency as each generated magnetic field. For example, a bandpass filter or a tuned electrical circuit could be included in the signal detector to isolate the portion of the sensor signal derived from the generated magnetic fields. The signal detector can thereby filter out signals due to e.g. remanant magnetic fields or stray magnetic fields and signal of other (unwanted) frequencies.

A phase sensitive detector may be included in the detector to detect a change in the phase of a signal output by the sensor. A phase sensitive detector may be used as a narrow bandpass filter to measure amplitude at a chosen frequency. The detector may include a filter and a rectifier for filtering and rectifying the signal output by the sensor, and a DC voltage detector to detect the filtered and rectified signal.

By being capable of generating a varying test magnetic field whilst remaining stationary relative to the casing borehole, a locator according to the present invention is insensitive to residual or stray permanent magnetisations of the casing or the surrounding environment which do not alternate at the frequency of the generated magnetic field(s).

Whilst a locator according to the present invention is primarily intended to be used to locate casing collars, such a locator can be made sufficiently sensitive that it can detect other features of the casing, such as perforations and corrosion holes. Therefore, a casing position locator according to the present invention is not limited to a locator used exclusively for the detection of the borehole casing collar.

Aspects and embodiments of the present invention will now be illustrated, by way of example, with reference to the accompanying figures. Further aspects and embodiments will be apparent to those skilled in the art.

BRIEF DESCRIPTION OF THE DRAWINGS

The present disclosure is described in conjunction with the appended figures.

DETAILED DESCRIPTION AND EXAMPLES

Figure 1:
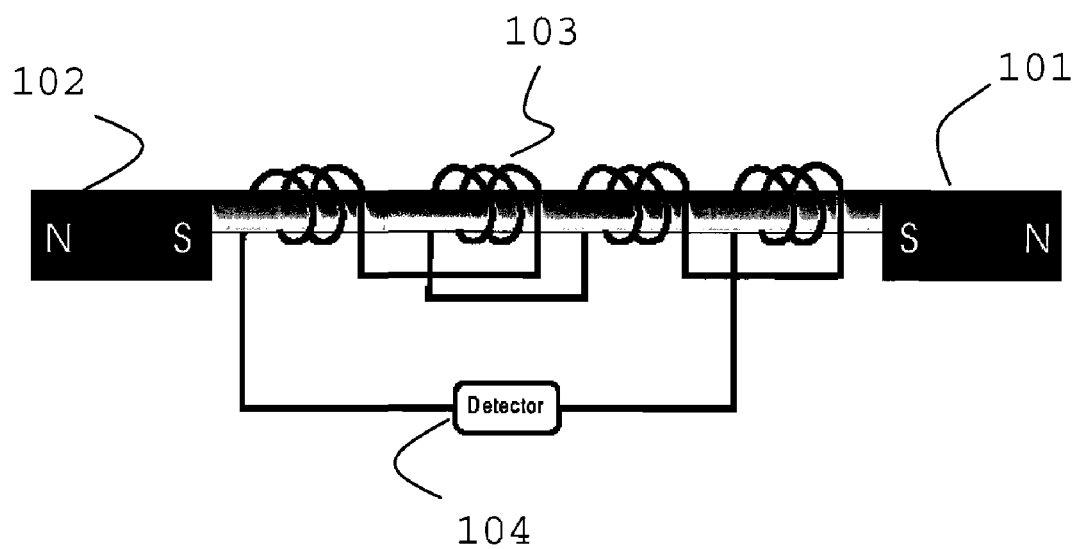
FIG. 1 shows an example of a conventional CCL according to the prior art.
Figure 2:
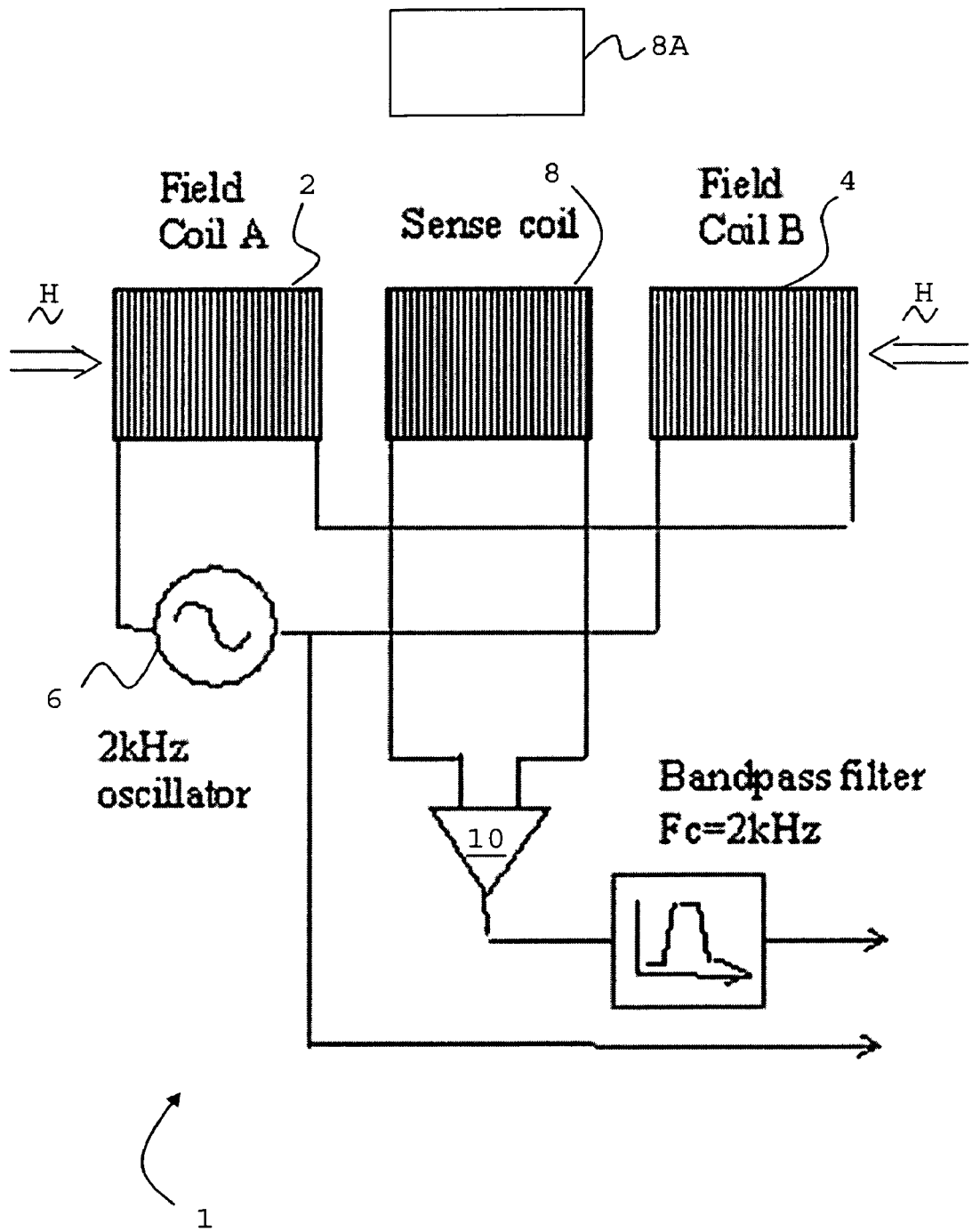
FIG. 2 shows an example of a locator according to the present invention.

A locator 1 according to the present invention is shown in FIG. 2, the locator 1 generates in use its own dynamic (or oscillating) test magnetic field. The test magnetic field is a combination of (at least two) dynamic (or oscillating) magnetic fields (H) respectively generated by the (at least two) magnetic field generators 2, 4.

Each generator shown in FIG. 2 includes an electromagnetic coil. However, any magnetic field generator capable of providing a dynamic (oscillating) magnetic field, e.g. a time-varying magnetic field, at a predetermined frequency is suitable. Preferably, each of the coils 2, 4 includes a magnetizable core, or former, (not shown) formed of e.g. iron or a ferrite material.

The coils 2, 4 are provided (in use) with current from an oscillator 6. Preferably, each coil 2, 4 is supplied with current from the same oscillator 6 as shown in FIG. 2. However, each coil 2, 4 could be supplied with current from a respective oscillator 6—each oscillator preferably driving the respective coil at the same frequency. In the shown example, the oscillator drives the coils 2,4 to generate respective dynamic magnetic fields oscillating at 2 kHz.

The coils 2, 4 and the or each oscillator 6 are arranged to generate respective fields in substantial opposition in order that the respective fields combine to substantially cancel each other out and thereby provide a substantial null point or region (or null plane)—preferably between the respective coils 2, 4—in the resultant test dynamic magnetic field.

A sensor such as an electromagnetic sense coil 8 is located in the test dynamic magnetic field, preferably between the coils 2, 4. The sense coil outputs (in use) a signal to a detector 10. In certain aspects a solid state device 8A may be used as the sensor. The solid state device may comprise a Hall effect device, GMR device or the like. The solid state device 8A may provide an output signal to the detector 10.

In a preferred embodiment, the sense coil 8 is located at the null point of the magnetic field when there is substantial uniform permeability surrounding the locator. In other words, in the absence of any external magnetic interaction which affects the location of the null point with respect to the field generators and/or the sensor (e.g. the sense coil), (at least a portion of) the sensor and the null point are preferably substantially co-existent.

Positioning the sense coil 8 in the null point can be done by mechanically maneuvering the sense coil until a null signal is produced. Alternatively, the sense coil 8 could be arbitrarily positioned at the null point (e.g. between the coils 2, 4) by actively driving the or each (respective) field coils 2, 4 so that the sense coil signal is at a minimum.

If the fields produced by the field coils 2, 4 are perfectly symmetrical, and the sense coil 8 has been uniformly wound, no signal should be induced in the sense coil 8. However, in practice, due to small imperfections in the respective generating and sensing coils there will always be a small signal from the sense coil. So, the null point or null region of the field may not be a point or region where the dynamic or oscillating test magnetic field is absolutely zero, but it may be a minimum value. Likewise, the sensor, such as the sense coil 8, may always output a minimum, non-zero, signal even when it is co-existent with the null point.

Any variation in the flux linkage between the field coils 2, 4 and the sense coil 8, e.g. due to a change in the permeability of the environment surrounding the locator, will cause a change in the dynamic test magnetic field detectable by the sense coil 8 and therefore an increase in the sense coil signal voltage and maybe a change in phase. As the asymmetry in permeability alters one of the generated dynamic magnetic fields to a greater or lesser degree than (each of) the other generated dynamic magnetic field(s), the null point moves to a new location where the relatively stronger and weaker generated dynamic magnetic fields cancel each other out.

Figure 3:
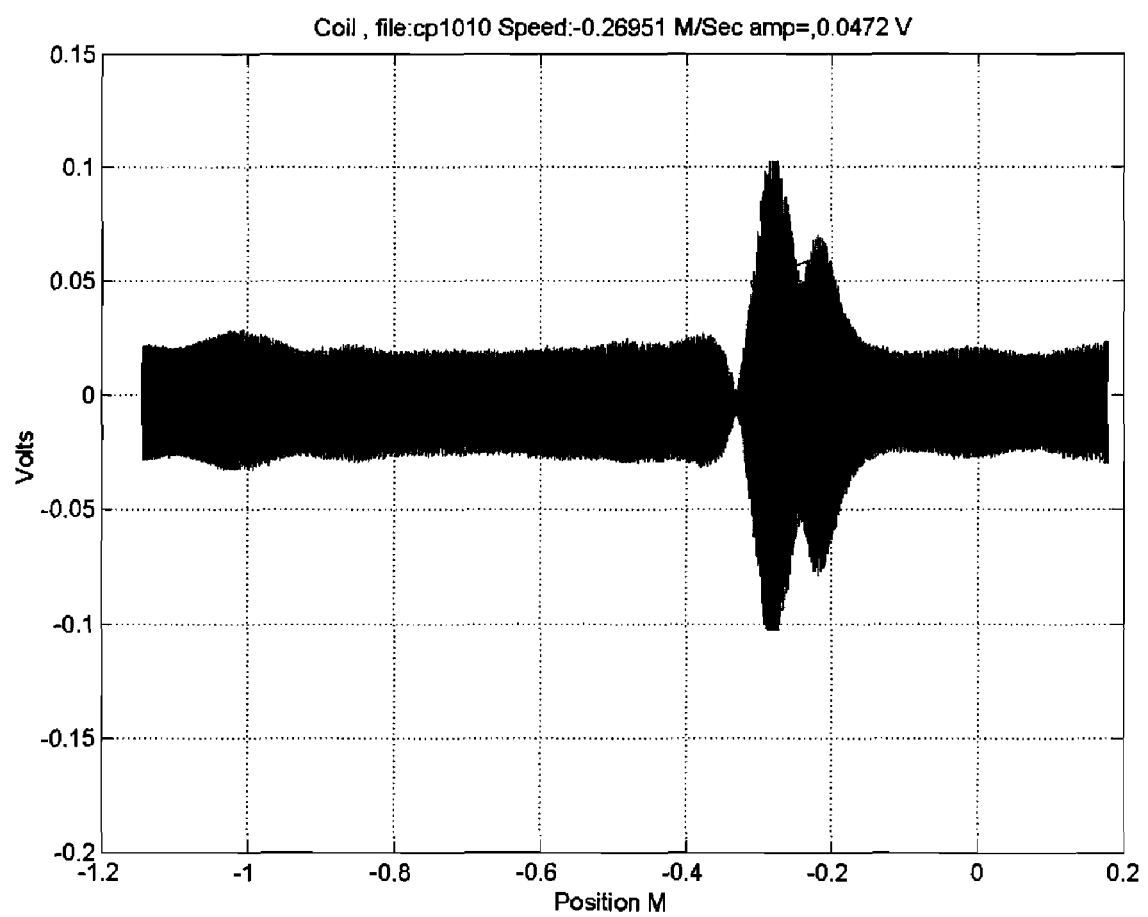
FIG. 3 shows an example of a signal indicating the presence of a borehole casing feature.

Consequently, in the preferred embodiment, the null point moves away from the sense coil 8. The sense coil 8 therefore detects a larger rate of change of flux. The sense coil 8 output signal reflects this increase as shown in e.g. FIG. 3.

Where a sensor which is capable of detecting absolute field strengths is used, such as a Hall effect device or a GMR device etc., the sensor would detect an absolute change in the field strength from the substantially zero field of the null point to a larger field strength indicating that the null point has moved.

In an alternative embodiment, the signal indicating that the null point has moved can be used to control one or more of the magnetic field generators (e.g. coils 2, 4) to alter the respective generated dynamic magnetic field to bring the null point back to the sensor—e.g. by minimizing the rate of change of flux (or absolute field—depending on the sensor used) detected by the sensor. Monitoring the control signal to the or each generator, e.g. by monitoring the output of the oscillator 6 to the or each coil 2, 4, provides an indication of the presence, and extent, of the asymmetry of the magnetic permeability.

As the field alternates at e.g. 2 kHz in the preferred embodiment the sense signal will be a 2 kHz a.c. voltage whose phase (relative to the driving oscillator) will depend on whether the flux linkage originates predominantly from field coil 2 or 4. So, the phase difference between the detected signal and the or each generated dynamic magnetic field indicates the presence and location of a magnetic permeability asymmetry.

As the locator passes a tubing joint, the change in permeability in the tubing will alter the flux linkage between the field coils 2, 4 and the sense coil 8. As it is the change in permeability that causes the change in the detected field (or rate of change of flux), it is independent of the speed at which the locator passes e.g. a tubing joint.

The sense coil signal can be band-passed filtered to remove any other frequency components from the signal output by the sense coil 8. Therefore, although emf voltages will be generated in the sense coil 8 as it passes through existing magnetic fields, these can easily be filtered out of the signal and eliminated.

To avoid repetition the present invention has been described by way of example, in which the field generators include electromagnetic coils 2, 4 and the sensor includes an electromagnetic sense coil 8. However, the use of electromagnetic coils is not essential.

While the invention has been described in conjunction with the exemplary embodiments described above, many equivalent modifications and variations will be apparent to those skilled in the art when given this disclosure together with the documents mentioned herein, which are all incorporated herewith by reference. Accordingly, the exemplary embodiments of the invention set forth above are considered to be illustrative and not limiting. Various changes to the described embodiments may be made without departing from the spirit and scope of the invention.

What is claimed is:

1. A method for determining structural features of a borehole casing, comprising:
    using a first field generator to generate a first dynamic magnetic field;
    using a second field generator to generate a second dynamic magnetic field;
    configuring the first and the second dynamic field generators such that the first and the second dynamic field generators produce a dynamic magnetic test field, wherein the test field includes a magnetic field null point where the first and the second dynamic magnetic fields substantially cancel each other out;
    passing the first and the second dynamic field generators through the borehole casing; and
    sensing at least one of a change in location of the null point or a change in magnetic field strength at the null point resulting from a change in permeability of the casing;
    using at least one of the sensed change in the location of the null point or the change in the magnetic field strength at the null point to detect changes in the permeability of the casing; and
    using the changes in the permeability to determine the structural features of the casing.

2. The method of claim 1, wherein the step of sensing comprises positioning a sensor such that there is flux linkage between the first and second field generators and the sensor.

3. The method of claim 2, wherein the sensor is positioned at the null point.

4. The method of claim 2, wherein in use the sensor outputs a signal indicative of a strength of the magnetic field proximate to the sensor.

5. The method of claim 2, including a phase sensitive detector to detect a change in at least the phase of said signal.

6. The method of claim 1, further comprising:
    adjusting at least one of the first and the second field generators to alter the location of the null point.

7. The method of claim 2, further comprising:
    adjusting at least one of the first and the second field generators in response to a signal output from the sensor.

8. The method of claim 2, wherein the sensor is located between the first and second field generators.

9. The method of claim 2, wherein an output signal from the sensor provides an indication of an asymmetry in the permeability of the casing.

10. A casing position locator according to claim 1, wherein the sensor includes an electromagnetic coil.

11. The method of claim 2, wherein the sensor comprises a solid state device capable of detecting a magnetic field.

12. The method of claim 2, wherein the sensor comprises a Hall effect device and/or a giant magnetoresistance device.

13. The method of claim 1, further comprising;
    varying the magnitude of the first and the second dynamic magnetic fields at a predetermined frequency.

14. The method of claim 13, wherein the predetermined frequency is between 0.1 Hz and 10kHz.

15. The method of claim 13, wherein the predetermined frequency is between 0.1 Hz and 2kHz.

16. The method of claim 12, further comprising:
    using a band pass filter to filter a signal output from the sensor, wherein an operating frequency of each of the first and the second dynamic magnetic fields is within the pass band of the band pass filter.

17. The method of claim 2, wherein the sensor is sensitive to changes in the permeability of the casing independent of a rate at which the first and the second dynamic field generators are passed through the casing.

* * * * *